(12) United States Patent
Jagiella et al.

(10) Patent No.: US 8,715,473 B2
(45) Date of Patent: May 6, 2014

(54) METHOD FOR DETERMINING ION CONCENTRATION OR CONCENTRATION OF A SUBSTANCE IN A SOLUTION

(75) Inventors: Manfred Jagiella, Nurtingen-Reudern (DE); Detlev Wittmer, Maulbronn (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 214 days.

(21) Appl. No.: 13/224,388

(22) Filed: Sep. 2, 2011

(65) Prior Publication Data

US 2012/0055814 A1  Mar. 8, 2012

(30) Foreign Application Priority Data

Sep. 3, 2010  (DE) .......................... 10 2010 040 264

(51) Int. Cl.
*G01N 27/414* (2006.01)
(52) U.S. Cl.
USPC .......................................... 204/406; 257/253
(58) Field of Classification Search
USPC ........................ 204/406, 416–420; 257/253
See application file for complete search history.

(56) References Cited

U.S. PATENT DOCUMENTS

| | | | |
|---|---|---|---|
| 4,701,253 A * | 10/1987 | Ligtenberg et al. | ........... 204/416 |
| 6,682,999 B1 | 1/2004 | Mucha | |
| 7,276,749 B2 | 10/2007 | Martin | |
| 2001/0008918 A1 | 7/2001 | Lohs et al. | |
| 2006/0121670 A1 | 6/2006 | Stasiak | |
| 2007/0212681 A1 | 9/2007 | Shapiro | |
| 2010/0301398 A1* | 12/2010 | Rothberg et al. | ............. 257/253 |

FOREIGN PATENT DOCUMENTS

| EP | 2 340 852 | 7/2011 |
|---|---|---|
| WO | WO 2005/073706 | 8/2005 |
| WO | 2010047804 A1 | 4/2010 |

OTHER PUBLICATIONS

German Search Report.
Herrmann et al., "The influence of different methods of disinfection on the function of electrochemical sensors", Sensors and Actuators B, vol. 69, 2000, pp. 164-170.

* cited by examiner

*Primary Examiner* — J. Christopher Ball
(74) *Attorney, Agent, or Firm* — Bacon & Thomas, PLLC

(57) ABSTRACT

Method for determining ion concentration or concentration of a substance in a solution by means of an ion selective, field effect transistor or an ion sensitive sensor having an EIS structure. The method comprises steps as follows: at least at a predetermined point in time of a first measuring phase, the potential lying on the electrode is sensed relative to a reference potential; before beginning a sterilization- and/or cleaning phase following the first measuring phase, the last voltage sensed during the first measuring phase is stored; and at the beginning of a second measuring phase following the sterilization- and/or cleaning phase, is the voltage stored during the sterilization phase is applied on the electrode.

16 Claims, 3 Drawing Sheets

METHOD FOR DETERMINING ION CONCENTRATION OR CONCENTRATION OF A SUBSTANCE IN A SOLUTION

TECHNICAL FIELD

The invention relates to a method for determining ion concentration or concentration of a substance in a solution by means of an ion selective, field effect transistor or an ion sensitive sensor, wherein the ion selective, field effect transistor or the ion sensitive sensor has an EIS structure, thus an Electrolyte Insulator Semiconductor structure, which comprises at least one semiconductor substrate, a layer of substrate oxide and a sensor layer. In the intermediate region between the substrate oxide and the sensor layer, an externally accessible electrode is provided. Furthermore, the invention relates to a corresponding ion selective, field effect transistor or ion sensitive sensor.

BACKGROUND DISCUSSION

Ion selective, field effect transistors or ion sensitive sensors are applied for measuring ion concentrations or for measuring special substance concentrations in solutions with different compositions and different conductivities.

The sensitive layers of ion selective, field effect transistors are almost exclusively formed by amorphous layers of e.g. simple metal oxides, as e.g. $Ta_2O_5$, $Al_2O_3$, $TiO_2$, $HfO_2$, simple metal nitrides or double metal oxide mixtures such as e.g. TaAlO and ZrAlO or combinations of two different amorphous metal oxide layers, which always have $SiO_2$ as base material. A large number of additionally suited materials, which are available for ISFETs as a function of the respective application, are described in the not pre-published patent applications of the assignee, namely in the German patent application DE 102009002060.8, filed on Mar. 31, 2009, and in the International patent application PCT/EP2010/053275, filed on Mar. 15, 2010. All there named options of material compositions are expressly incorporated by reference in the disclosure of the present patent application.

ISFETs are well established examples for sensors having an EIS structure, wherein here the insulator forms the ion sensitive gate insulator of the field effect transistor. ISFETs are widely applied for the continuous detection of concentrations and for pH measurements for environmental monitoring, in industrial automation technology, in the foods industry and in biochemistry and medical technology. The advantages of ISFETs lie in their glassless construction, in their highly precise registration of concentrations, in their fast start-up and in their minimum long time drift combined with an acceptable price/power ratio.

In the case of so-called LAPS—Light Addressable Potentiometric Sensors—by means of a modulated light signal, photoelectrons are produced in the semiconductor material of an EIS structure. The generating of the photoelectrons is dependent on the particular properties of the electrolyte. A basic description of LAPS is given in the article, "Light Addressable Potentiometric Sensor For Biochemical Systems", Hafeman et al., Science 240 (1988), Pgs. 1182-1185.

In automation technology, especially in process automation technology, ion selective, field effect transistors or ion sensitive sensors are often subjected to wearing sterilization- and/or cleaning-processes. Referenced here are especially SIP—(Sterilization In Process) processes and CIP (Cleaning In Process) processes. In the case of CIP processes, which are applied frequently in the foods industry, for example, for cleaning pipeline systems and which are often absolutely required, the ion selective, field effect transistors or the ion sensitive sensors are typically exposed for a time period of about a half hour to strong acid or base solutions, which have a temperature of about 85° C. For SIP processes, which serve, for example, for sterilizing pipeline systems, the installed sensors are heated for a certain time period to about 130° C. Through these processes, the ion selective, field effect transistors or ion sensitive sensors are unavoidably influenced as regards their functionality and accuracy of measurement: After the CIP or SIP process, is the sensor is often in a state, which deviates from the state, which the sensor had before the CIP or SIP process, and which without knowledge of this change would lead to bad measurements.

WO 2005/073706 A1 discloses an improved gate configuration for an ISFET pH sensor. Especially, here, a sensitive layer of tantalum oxide is applied on an aluminum layer. While the sensitive layer of tantalum oxide assures a high measurement quality, the aluminum layer increases the life of the ISFET pH sensor, since it prevents penetration of the measured liquid into the substrate oxide layer.

Problematic in the case of CIP and SIP processes is that the charging characteristic of an ion selective, field effect transistor or an ion sensitive sensor is changed. This leads to fluctuations in the measurement results, which are not caused by a corresponding change in the composition of the medium to be determined or monitored.

SUMMARY OF THE INVENTION

An object of the invention is to provide a method for determining ion concentration or concentration of a substance in a solution and to provide a correspondingly embodied, ion selective, field effect transistor, or a correspondingly embodied, ion sensitive sensor, which after a SIP or CIP process have the same state as before the sterilization- or cleaning process.

The object is achieved, as regards method, by the following method steps:
  at least at a predetermined point in time of a first measuring phase, the potential lying on the electrode is sensed relative to a reference potential;
  before beginning a sterilization- and/or cleaning phase following the first measuring phase, the last voltage sensed during the first measuring phase is stored;
  at the beginning of a second measuring phase following the sterilization phase, the voltage stored during the sterilization phase is applied to the electrode.

The electrode, on which the potential is sensed, can be embodied in any desired manner. It can be e.g. a layer having a continuous expanse, a lattice structure, a layer with any kind of perforations or even a strip shaped coating. The material of the electrode can, in principle, be any material with good conductivity. Especially advantageous is the case in which the material supplementally resistant to the measured liquid.

An advantageous embodiment of the method of the invention provides that the first measuring phase, the sterilization- and/or cleaning phase and the second measuring phase repeat in predetermined time intervals. As already stated, SIP and CIP processes last around 30 minutes.

Furthermore, it is provided that the voltage on the electrode is sensed with high impedance. When thereby only a negligibly small electrical current flows, the accuracy of measurement of the sensor is not influenced by the method of the invention.

Especially advantageous in connection with the invention is when the point in time for the introduction of the next measuring phase, or for the introduction of the next sterilization phase, is ascertained based on the temperature curve and/or based on the pH curve. If e.g. a predetermined limit value is exceeded, or subceeded (fallen beneath), then this is interpreted as an indication of need for the next SIP or CIP process. Of course, it is also possible to define the temperature curve continuously.

In an advantageous form of embodiment, the method of the invention provides the opportunity, based on the voltages, which are sensed over the course of the measuring phases following one after the other, as well as directly before, during and after the sterilization phase or cleaning phase on the electrode, to perform an evaluation as regards the state or as regards the remaining service life of the ion selective, field effect transistor or the ion sensitive sensor. With the solution of the invention, it is, thus, possible to gain information relevant for predictive maintenance.

In this connection, it is, moreover, especially advantageous, when, in defined intervals, an alternating voltage is applied to the electrode and when, based on the response signal sensed on the electrode, an impedance spectrogram is ascertained. In this way, for example, changed electrical properties of the sensor or changed charge carrier densities in the sensor can be recognized. Alternatively, an option is to apply a predetermined voltage signal curve to the electrode and based on the response signal of the electrode to obtain information concerning the corresponding properties of the sensor. Both methods are suitable for gaining information concerning the instantaneous state or the remaining service life to be expected for the ion selective, field effect transistor or the ion sensitive sensor.

Furthermore, the method provides, based on the voltage curve on the electrode measurable during the cleaning- and/or sterilization phase, to obtain information concerning the current state of the sensor as well as its service life to be expected.

The object is achieved as regards the ion selective, field effect transistor or the ion sensitive sensor by features including that a controlled circuit arrangement is provided having an impedance converter and a sample/hold circuit connected in series with the impedance converter. On the first input of the impedance converter lies during the first measuring phase the electrode potential, while on the inverting input the reference potential is applied. The reference potential can be e.g. ground potential. The sample/hold-circuit stores in a memory element during the sterilization phase the respective last voltage lying on the electrode during the first measuring phase and freezes this value. At the beginning of the second measuring phase following the sterilization phase, the stored, or frozen, voltage is applied back on the electrode. Thus, it is assured that the conditions for a following measuring are identical with the conditions, which reigned in the case of the preceding measuring. The same charge conditions are present on the sensor before and after the SIP or CIP process. In principle, it is sufficient, when the charge on the electrode at a point in time before the SIP or CIP process is measured. Preferably, there occurs, however, a continuous registering of the charge state during the measuring phases.

An advantageous embodiment of the ion selective, field effect transistor or the ion sensitive sensor of the invention provides two controllable switches, wherein the first switch is opened during the measuring phase and wherein the second switch is closed during the measuring phase, so that the sample/hold-circuit, in each case, stores in the memory element the last voltage sensed on the electrode.

Moreover, it is provided that the first switch and the second switch are opened during the sterilization phase, so that the last voltage sensed on the electrode before the opening of the second switch is stored in the memory element, or frozen.

In connection with the ion selective, field effect transistor or ion selective sensor, it is, furthermore, provided that the first switch is closed at the beginning of the second measuring phase following the sterilization- and/or cleaning phase and that the second switch is opened at the beginning the second measuring phase, so that the voltage stored in the memory element, or frozen, lies on the electrode. Preferably, the switches are electronic switches, wherein the control of the time curve of the circuit arrangement occurs via a microprocessor.

It has been found to be especially advantageous, when the semiconductor substrate is silicon, in the case of which the substrate oxide is silicon oxide and the sensor layer is hafnium oxide or tantalum pentoxide. Such sensor layers provide a high measurement quality.

A preferred embodiment provides that the ion selective, field effect transistor or the ion sensitive sensor and the circuit arrangement are arranged on a sensor chip.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

Figure 1A:
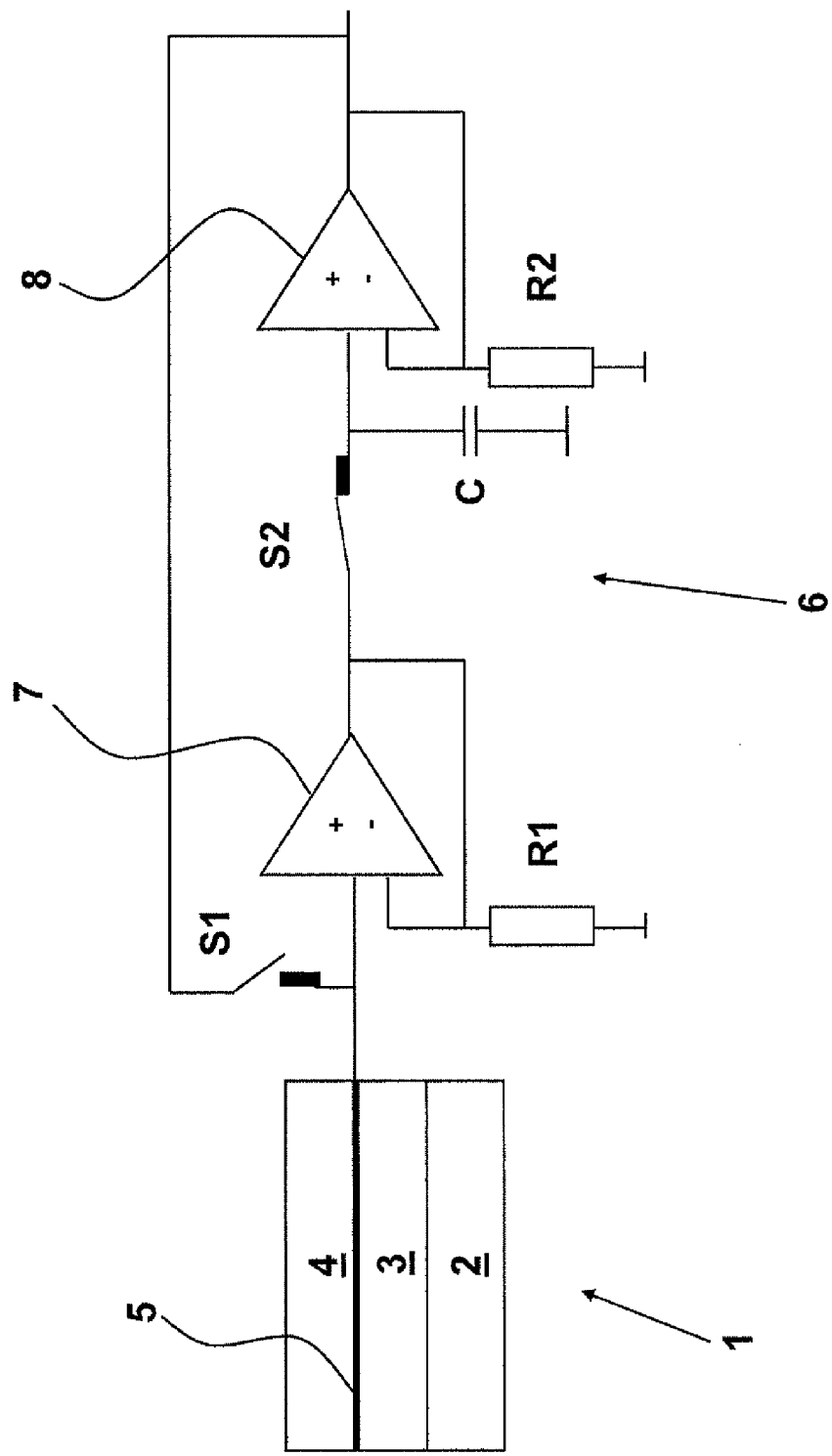
FIGS. 1a, 1b and 1c illustrate successively the individual method steps, which define an advantageous form of embodiment of the method of the invention. Furthermore, the figures show a preferred embodiment of the ion selective, field effect transistor, or the ion sensitive sensor, 1 for determining ion concentration or concentration of a substance in a solution.
Figure 1:
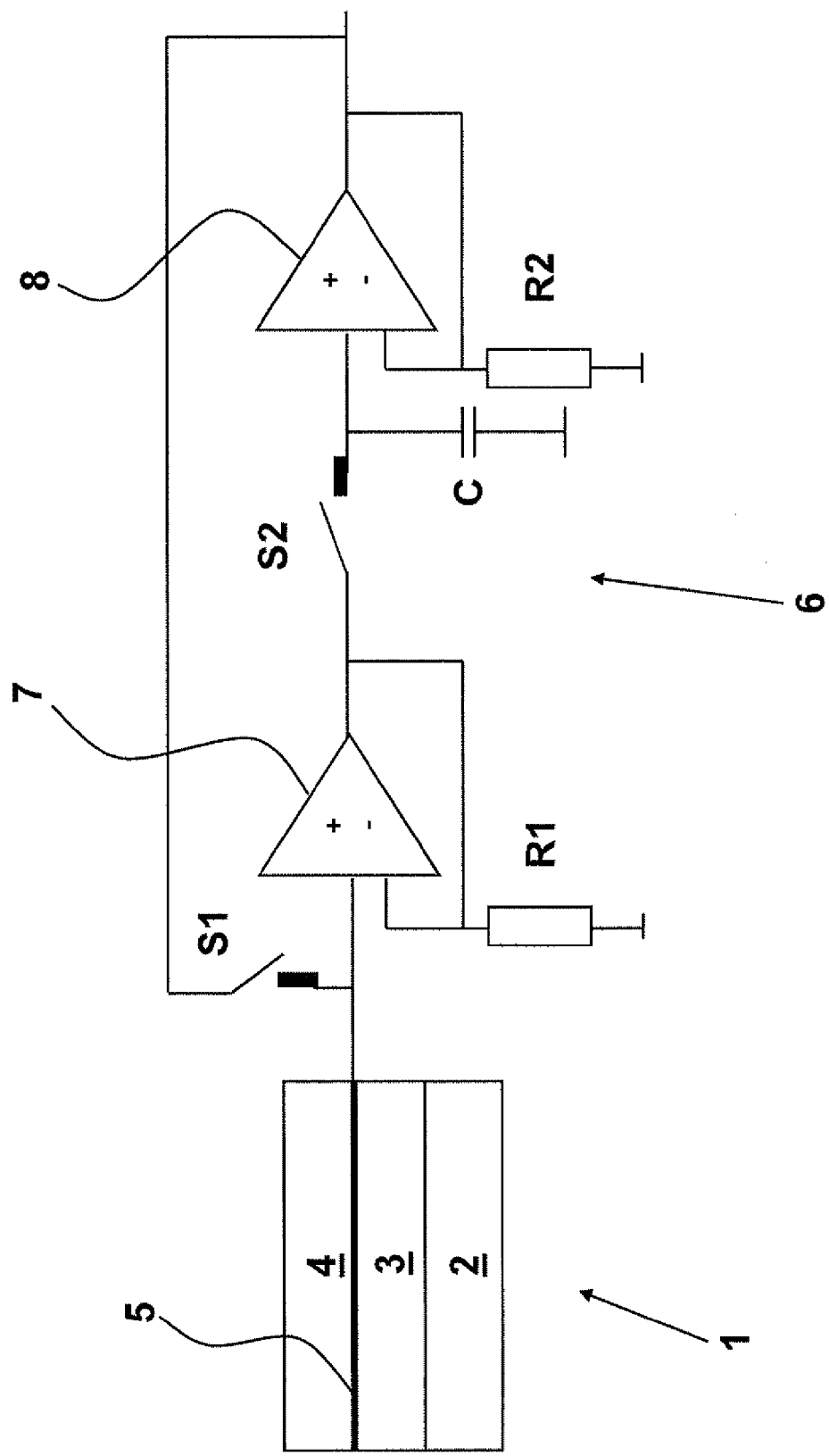
Figure 1:
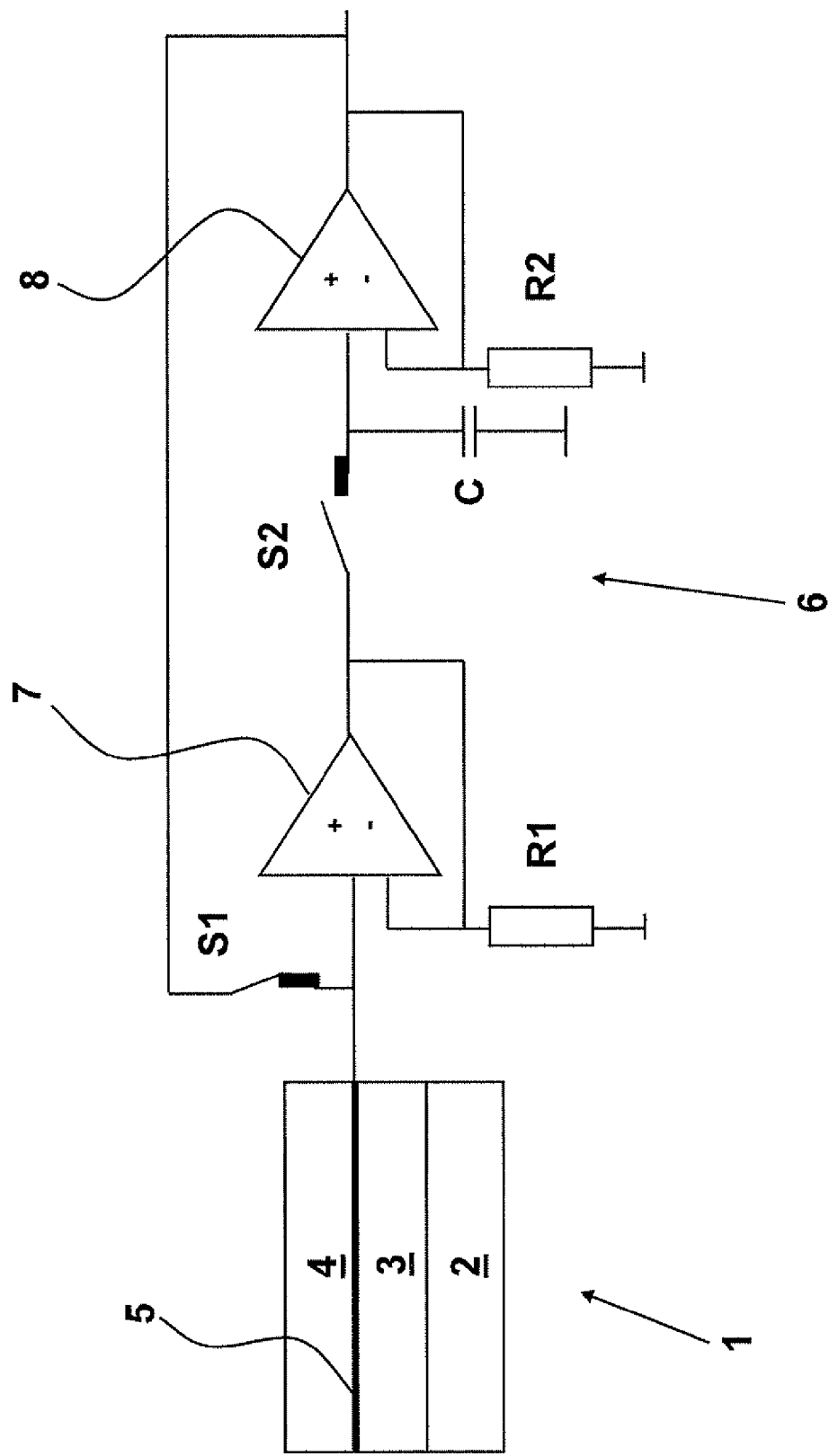

The ion selective, field effect transistor, or the ion sensitive sensor, 1 has an EIS structure, thus an Electrolyte Insulator Semiconductor structure. In the illustrated case, sensor 1 has a minimum required layer structure: A semiconductor substrate 2, a layer of substrate oxide 3 and a sensor layer 4. Usually, the semiconductor substrate 2 is silicon, the substrate oxide 3 is silicon oxide and the sensor layer 4 is tantalum pentoxide and/or hafnium oxide. A plurality of sensor layers 4 can be used in connection with the invention. Some are mentioned explicitly in the introduction of the description. Of course, the listing in the introduction of the description is not exclusive. Furthermore, the layer structure of the sensor 1 can also be embodied in any known type and manner.

According to the invention, in the intermediate region between the substrate oxide 3 and the sensor layer 4 an externally accessible electrode 5 is arranged. Electrode 5 can be formed and embodied in any manner. It serves for the purpose of holding the potential between the sensor layer 4 and the layer of the sensor 1 adjoining the electrode 5 on the oppositely lying side at a predetermined, constant value.

The figures show how, by way of example, the individual method steps of the method of the invention can be implemented. For this, a circuit arrangement 6 is used, which is essentially composed of an impedance converter 7 and a sample/hold circuit 8. Lying on the first input of the impedance converter 7 is the potential of the electrode 5 and on the inverting input of the impedance converter 7 the reference potential. The reference potential is ground, for example. Connected in series with the impedance converter 7 is the sample/hold circuit 8. Furthermore, the circuit arrangement 6 includes two switches S1, S2, a capacitor C and two resistors R1, R2.

The circuit arrangement 6 is so controlled by means of a microprocessor (not separately illustrated in the figures) that it stores in the memory element, or capacitor, C, in each case, the last voltage lying on the electrode 5 during the preceding measuring phase. At the beginning of the measuring phase following the cleaning- or sterilization phase, the stored voltage is applied back on the electrode 5.

FIG. 1a shows the first method step, when, thus, at a predetermined point in time of the first measuring phase, the voltage lying on the electrode 5 is sensed relative to the reference potential. For this, the first switch S1 is opened during the first measuring phase; the second switch S2 is closed during the first measuring phase. Thus, the sample/hold circuit 8 stores in the memory element C, in each case, the last voltage sensed on the electrode 5.

FIG. 1b shows the following, second method step. Before beginning a sterilization- and/or cleaning phase following the first measuring phase, the last voltage sensed during the first measuring phase is stored. For this, the first switch S1 and the second switch S2 are opened, so that the last voltage sensed on the electrode 5 before the opening of the second switch S2 is stored, or frozen, in the memory element C.

The third method step is shown in FIG. 1c. At the beginning of the following, second measuring phase, the voltage stored during the cleaning- or sterilization phase is applied to the electrode 5. In order to achieve this, the first switch S1 is closed at the beginning of the second measuring phase following the cleaning- or sterilization phase, while the second switch S2 is opened at the beginning of the second measuring phase, so that the voltage frozen in the memory element C lies on the electrode 5.

The respective switching points in time for the switch S1, S2 are ascertained by the microprocessor, for example, based on the temperature curve and/or based on the pH value curve of the solution in contact with the sensor 1. The temperature must be ascertained via a temperature sensor. Likewise, an option is that the microprocessor correspondingly switches the switches S1, S2, when it outputs or receives the control signals for introducting the measuring- and cleaning/sterilization phases.

LIST OF REFERENCE CHARACTERS 1 ion selective, field effect transistor or ion sensitive sensor
2 semiconductor substrate
3 semiconductor oxide
4 sensitive layer
5 electrode
6 circuit arrangement
7 impedance converter
8 sample/hold circuit
S1 first switch
S2 second switch
C capacitor

The invention claimed is:

1. A method for determining ion concentration or concentration of a substance in a solution by means of an ion selective, field effect transistor, or an ion sensitive sensor, with an EIS structure, thus an Electrolyte Insulator Semiconductor structure, which includes at least one semiconductor substrate, a layer of substrate oxide and a sensor layer, wherein at least in an intermediate region between the substrate oxide and the sensor layer an externally accessible electrode is provided, wherein the method comprises the steps of:

at least at a predetermined point in time of a first measuring phase, the potential lying on the electrode is sensed relative to a reference potential;

before beginning a sterilization- and/or cleaning phase following the first measuring phase, the last voltage sensed during the first measuring phase is stored; and at the beginning of a second measuring phase following the sterilization- and/or cleaning phase, the voltage stored during the sterilization phase is applied to the electrode.

2. The method as claimed in claim 1, wherein:
the first measuring phase, the sterilization- and/or cleaning phase and the second measuring phase repeat in predetermined time intervals.

3. The method as claimed in claim 1, wherein:
the voltage on the electrode is sensed with high impedance.

4. The method as claimed in claim 1, wherein:
based on the voltages, which are sensed on the electrode over the course of measuring phases following one after the other, an evaluation as regards state, or as regards remaining service life, of the ion selective, field effect transistor, or the ion selective sensor, is performed.

5. The method as claimed in claim 1, wherein:
the point in time for introducing the next measuring phase, or for introducing the next sterilization phase, is ascertained based on a temperature curve and/or based on a pH value curve.

6. The method as claimed in claim 1, wherein:
in defined intervals, an alternating voltage is applied to the electrode and wherein based on the response signal sensed on the electrode an impedance spectrogram is ascertained.

7. The method as claimed in claim 1, wherein:
a predetermined voltage signal curve is applied to the electrode; and
based on a response signal of the electrode information concerning instantaneous state or remaining service life of the ion selective, field effect transistor or the ion selective sensor is gained.

8. The method as claimed in claim 1, wherein:
after terminating the sterilization- and/or cleaning phase, the voltage lying on the electrode is sensed relative to a reference potential, before the voltage stored during the sterilization phase is applied to the electrode: and
the measured voltage is taken into consideration for ascertaining state and/or remaining service life of the ion selective, field effect transistor, or the ion selective sensor.

9. The method as claimed in claim 1, wherein:
during the sterilization- and/or cleaning phase, at least one point in time, the voltage lying on the electrode is sensed relative to a reference potential; and
based on at least one ascertained voltage, in given cases by comparison with voltage values, which were ascertained during previous sterilization- and/or cleaning phases, information concerning state and/or remaining service life of the ion selective, field effect transistor, or the ion selective sensor, is gained.

10. An ion selective, field effect transistor, or ion sensitive sensor for performing a method at least at a predetermined point in time of a first measuring phase, the potential lying on the electrode is sensed relative to a reference potential;

at least at a predetermined point in time of a first measuring phase, the potential lying on the electrode is sensed relative to a reference potential;

before beginning a sterilization- and/or cleaning phase following the first measuring phase, the last voltage sensed during the first measuring phase is stored; and at the beginning of a second measuring phase following the sterilization- and/or cleaning phase, the voltage stored during the sterilization phase is applied to the electrode, the transistor comprising:

a controlled circuit arrangement having an impedance converter, on whose first input the electrode potential is applied during the first measuring phase and on whose inverting input a reference potential is applied;

a sample/hold circuit connected in series with said impedance converter for storing and freezing in a memory element during the cleaning- and/or sterilization phase the last voltage applied during the first measuring phase on an electrode, and for applying on said electrode at the beginning of the second measuring phase following the sterilization phase the stored, frozen voltage, wherein:

the transistor has an Electrolyte Insulator Semiconductor structure with a minimum required layer structure of: semiconductor substrate, a layer of substrate oxide, and a sensor layer; and in the intermediate region between said substrate oxide and said sensor layer, said externally accessible electrode is arranged.

11. The ion selective, field effect transistor, or ion sensitive sensor, as claimed in claim 10, further comprising:

two controllable switches, wherein:

the first switch is opened during the measuring phase; and the second switch is closed during the measuring phase, so that said sample/hold circuit, in each case, stores in said memory element the last voltage sensed on said electrode.

12. The ion selective, field effect transistor, or ion sensitive sensor, as claimed in claim 10, wherein:

said first switch and said second switch are opened during the sterilization phase, so that the last voltage sensed on said electrode before the opening of said second switch is stored, or frozen, in said memory element.

13. The ion selective, field effect transistor, or ion sensitive sensor, as claimed in claim 10, wherein:

said first switch is closed at the beginning of the second measuring phase following the sterilization phase; and said second switch is opened at the beginning of the second measuring phase, so that the voltage frozen in said memory element is applied on said electrode.

14. The ion selective, field effect transistor, or ion sensitive sensor, as claimed in claim 10, wherein:

a semiconductor substrate comprises silicon, in the case of which the substrate oxide is silicon oxide, and a sensor layer is hafnium oxide or tantalum pentoxide.

15. The ion selective, field effect transistor, or ion sensitive sensor, as claimed in claim 10, further comprising:

a microprocessor, which controls the circuit arrangement as a function of time.

16. The ion selective, field effect transistor, or ion sensitive sensor, as claimed in claim 10, wherein:

the ion selective, field effect transistor and the circuit arrangement are arranged on a sensor chip.

* * * * *